US008398959B2

(12) United States Patent
Yang et al.

(10) Patent No.: US 8,398,959 B2
(45) Date of Patent: Mar. 19, 2013

(54) COMPOSITIONS AND METHODS FOR IMPARTING A SUNLESS TAN WITH FUNCTIONALIZED ADJUVANTS

(75) Inventors: Xiaoxia Yang, Shanghai (CN); Jun-Cheng Zhu, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/305,961

(22) Filed: Nov. 29, 2011

(65) Prior Publication Data
US 2012/0141393 A1    Jun. 7, 2012

(30) Foreign Application Priority Data

Dec. 6, 2010   (WO) ................. PCT/CN2010/001964

(51) Int. Cl.
*A61K 8/00*   (2006.01)
(52) U.S. Cl. .......................................... 424/59
(58) Field of Classification Search ...................... 424/59
See application file for complete search history.

(56) References Cited

U.S. PATENT DOCUMENTS

| | | | |
|---|---|---|---|
| 4,104,403 A | 8/1978 | Barker | |
| 4,385,049 A | 5/1983 | Cuca | |
| 4,405,616 A | 9/1983 | Rajadhyaksha | |
| 4,551,148 A | 11/1985 | Riley et al. | |
| 4,606,913 A | 8/1986 | Aronson | |
| 4,808,610 A | 2/1989 | Munayyer et al. | |
| 4,886,783 A | 12/1989 | Minaskanian | |
| 4,888,783 A | 12/1989 | Kojima | |
| 4,981,845 A | 1/1991 | Pereira | |
| 5,118,845 A | 6/1992 | Peck | |
| 5,131,911 A * | 7/1992 | Lang et al. ............ | 8/405 |
| 5,232,688 A | 8/1993 | Ziegler et al. | |
| 5,387,417 A | 2/1995 | Rentsch | |
| 5,412,004 A | 5/1995 | Tachibana | |
| 5,523,075 A | 6/1996 | Fuerst et al. | |
| 5,612,044 A | 3/1997 | Suares et al. | |
| 5,645,822 A | 7/1997 | Meyere et al. | |
| 5,700,452 A | 12/1997 | Deckner et al. | |
| 5,720,948 A | 2/1998 | Brucks | |
| 5,750,092 A | 5/1998 | Meyer et al. | |
| 5,756,075 A | 5/1998 | Meyer | |
| 5,833,973 A | 11/1998 | Dobkowski | |
| 5,908,707 A | 6/1999 | Cabell | |
| 5,977,194 A | 11/1999 | Mork | |
| 6,033,648 A | 3/2000 | Candau | |
| 6,060,041 A | 5/2000 | Candau et al. | |
| 6,069,169 A | 5/2000 | Ptchelintsev et al. | |
| 6,147,131 A | 11/2000 | Mork | |
| 6,231,837 B1 | 5/2001 | Stroud et al. | |
| 6,303,834 B1 | 10/2001 | Mork | |
| 6,313,181 B1 | 11/2001 | Cohen | |
| 6,326,033 B1 | 12/2001 | Darmenton et al. | |
| 6,352,701 B1 | 3/2002 | Scholz et al. | |
| 6,383,503 B1 | 5/2002 | Bleckmann | |
| 6,399,046 B1 | 6/2002 | Schonrock et al. | |
| 6,423,626 B1 | 7/2002 | Srinivasan et al. | |
| 6,475,500 B2 | 11/2002 | Vatter | |
| 6,524,598 B2 | 2/2003 | Sunkel | |
| 6,548,050 B1 | 4/2003 | Bara | |
| 6,685,952 B1 | 2/2004 | Ma | |
| 6,696,049 B2 | 2/2004 | Vatter | |
| 6,699,488 B2 | 3/2004 | Deckner | |
| 6,747,115 B2 | 6/2004 | Sakuta | |
| 6,793,929 B2 | 9/2004 | Bleckmann | |
| 7,166,276 B2 | 1/2007 | Stephens et al. | |
| 7,175,835 B1 | 2/2007 | Simoulidis et al. | |
| 7,316,808 B2 | 1/2008 | Candau | |
| 7,416,735 B2 | 8/2008 | El-Nokaly et al. | |
| 7,462,363 B2 | 12/2008 | Braun | |
| 2002/0028184 A1 | 3/2002 | Sunkel | |
| 2002/0028223 A1 | 3/2002 | Vatter et al. | |
| 2002/0051755 A1 | 5/2002 | Candau et al. | |
| 2002/0106385 A1 | 8/2002 | Vatter | |
| 2002/0142018 A1 | 10/2002 | Scholz et al. | |
| 2003/0044365 A1 | 3/2003 | Candau | |
| 2003/0082119 A1 | 5/2003 | Golz-Berner et al. | |
| 2003/0108498 A1 | 6/2003 | Stephens et al. | |
| 2003/0170193 A1 | 9/2003 | Pate | |
| 2003/0211061 A1 | 11/2003 | Deckner | |
| 2003/0211069 A1 | 11/2003 | Deckner | |
| 2003/0228339 A1 | 12/2003 | El-Nokaly et al. | |
| 2004/0014653 A1 | 1/2004 | Smith | |
| 2004/0047819 A1 | 3/2004 | Hansenne et al. | |
| 2004/0076597 A1 | 4/2004 | Berens et al. | |

(Continued)

FOREIGN PATENT DOCUMENTS

CN    1816316 A        8/2006
CN    1816316A-ABS    8/2006

(Continued)

OTHER PUBLICATIONS

., 2004, Shin-Etsu-Silicone for Personal Care, Shin-Etsu Chemical Co., Ltd., ., 1-6.
Dussaud, May 30, 2003, Liquid Transport in the Networked Microchannels of the Skin Surface, Langmuir, 19, 7341-7345.
Shin Etsu, 2007, Silicone Products for Personal Care-Shin-Etsu Unique Materials, ShinEtsu Silicone, ., 1-20.
Shin-Etsu Chemical Co., Ltd., Feb. 1, 2002, Emulsifiers for Cosmetic Products, Shin-Etsu Silicones for Personal Care 2002 1.pdf, ., 1-6, Shin-Etsu Chemical Co., Ltd.
Co-pending Application: Applicant: Lou et al., U.S. Appl. No. 12/060,437, filed: Apr. 1, 2008.
Co-pending Application: Applicant: Lou et al., U.S. Appl. No. 12/402,238, filed: Mar. 11, 2009.
Co-pending Application: Applicant: Carnali et al., U.S. Appl. No. 12/627,566, filed: Nov. 30, 2009.
Co-pending Application: Applicant: Lou et al., U.S. Appl. No. 12/784,046, filed: May 20, 2010.
Co-pending Application: Applicant: Lou et al., U.S. Appl. No. 12/814,855, filed: Jun. 14, 2010.

(Continued)

Primary Examiner — Daniel Sullivan
Assistant Examiner — Rachael E Bredefeld
(74) Attorney, Agent, or Firm — Edward A. Squillante, Jr.

(57) ABSTRACT

Described are compositions and methods for imparting a sunless tan with functionalized adjuvants and a tanning agent like dihydroxyacetone. The functionalized adjuvants are pyrrole and/or indole derivatives functionalized with a substituent comprising a carbonyl group.

9 Claims, No Drawings

U.S. PATENT DOCUMENTS

| | | | |
|---|---|---|---|
| 2004/0086474 A1 | 5/2004 | Rabe et al. |
| 2004/0146472 A1 | 7/2004 | Nakanishi |
| 2004/0228821 A1 | 11/2004 | Sunkel et al. |
| 2004/0235693 A1 | 11/2004 | Wei |
| 2005/0002978 A1 | 1/2005 | Crook et al. |
| 2005/0008600 A1 | 1/2005 | Nakanishi |
| 2005/0089486 A1 | 4/2005 | Spindler |
| 2005/0118218 A1 | 6/2005 | Cassin |
| 2005/0169856 A1 | 8/2005 | Grollier |
| 2005/0175570 A1 | 8/2005 | Inoue |
| 2005/0191326 A1 | 9/2005 | Mleker |
| 2005/0238595 A1 | 10/2005 | Stella |
| 2006/0008426 A1 | 1/2006 | Doring |
| 2006/0010979 A1 | 1/2006 | Rubin |
| 2006/0013790 A1 | 1/2006 | Shimizu |
| 2006/0057927 A1 | 3/2006 | Kang |
| 2006/0078524 A1 | 4/2006 | Midha |
| 2006/0078527 A1 | 4/2006 | Midha |
| 2006/0079417 A1 | 4/2006 | Wagner et al. |
| 2006/0079422 A1 | 4/2006 | Midha |
| 2006/0100004 A1 | 5/2006 | Kim et al. |
| 2006/0111490 A1 | 5/2006 | Fonolla Moreno |
| 2006/0127344 A1 | 6/2006 | Zofchak |
| 2006/0171909 A1 | 8/2006 | Morrissey et al. |
| 2007/0009463 A1 | 1/2007 | Niebauer |
| 2007/0020217 A1 | 1/2007 | Themens |
| 2007/0067924 A1 | 3/2007 | Beck et al. |
| 2007/0173599 A1 | 7/2007 | Liu |
| 2007/0292373 A1 | 12/2007 | Russ et al. |
| 2008/0081057 A1 | 4/2008 | Chevalier |
| 2008/0279793 A1 | 11/2008 | Rudolph et al. |
| 2008/0279796 A1 | 11/2008 | Handrosch et al. |
| 2008/0299058 A1 | 12/2008 | Saito |
| 2008/0299156 A1 | 12/2008 | Fares |
| 2008/0311058 A1 | 12/2008 | Lou |
| 2009/0035241 A1 | 2/2009 | Cassin |
| 2009/0041688 A1 | 2/2009 | Dueva-Koganov et al. |
| 2009/0155321 A1 | 6/2009 | Harichian et al. |
| 2009/0155322 A1 | 6/2009 | Harichian et al. |
| 2009/0178209 A1 | 7/2009 | Koike et al. |
| 2009/0226498 A1 | 9/2009 | Flugge-Berendes |
| 2009/0247445 A1 | 10/2009 | Lou et al. |

FOREIGN PATENT DOCUMENTS

| | | |
|---|---|---|
| CN | 101068528 A | 5/2011 |
| DE | 10049041 A1 | 4/2002 |
| DE | 10049041Abstrac | 4/2002 |
| DE | 102004055541 | 5/2006 |
| DE | 102008006857 | 1/2009 |
| EP | 0009404 A2 | 4/1980 |
| EP | 0160430 | 11/1985 |
| EP | 0302147 A1 | 2/1989 |
| EP | 0500446 A1 | 8/1992 |
| EP | 810181 A2 | 12/1997 |
| EP | 818190 | 1/1998 |
| EP | 1864647BTransla B1 | 11/2001 |
| EP | 1210933 | 6/2002 |
| EP | 1352639 A1 | 10/2003 |
| EP | 1352639A1Transl | 10/2003 |
| EP | 1600144 A1 | 11/2005 |
| EP | 1741422 | 1/2007 |
| EP | 2087879 | 8/2009 |
| EP | 1864647 B1 | 11/2011 |
| GB | 1456530 | 2/1977 |
| GB | 1465528 | 2/1977 |
| GB | 1465529 | 2/1977 |
| GB | 2139919 | 11/1984 |
| GB | 2181737 | 4/1987 |
| JP | 57091733 | 6/1982 |
| JP | 11158032 | 6/1999 |
| JP | 11158032Transl | 6/1999 |
| JP | 2005314327 | 11/2005 |
| JP | 2005314327Trans | 11/2005 |
| KE | 57091733PAJABST | 6/1985 |
| WO | WO9217159 | 10/1992 |
| WO | WO9403148 | 2/1994 |
| WO | WO9415580 | 7/1994 |
| WO | WO9421221 | 9/1994 |
| WO | WO9526178 | 10/1995 |
| WO | WO9621721 | 7/1996 |
| WO | WO9733560 | 9/1997 |
| WO | WO9800098 | 1/1998 |
| WO | WO09955303 | 11/1999 |
| WO | WO0100141 | 1/2001 |
| WO | WO0189464 | 11/2001 |
| WO | WO03022235 | 3/2003 |
| WO | WO03075879 | 9/2003 |
| WO | WO03080005 A1 | 10/2003 |
| WO | WO2004105721 A1 | 12/2004 |
| WO | WO2005016302 A1 | 2/2005 |
| WO | WO2005016302A1 A1 | 2/2005 |
| WO | WO2005025505 A2 | 3/2005 |
| WO | WO2008013757 | 1/2008 |
| WO | WO2008155228 | 12/2008 |
| WO | WO2009053287A1 A1 | 4/2009 |
| WO | WO2009074513 A1 | 6/2009 |
| WO | WO2009121787 | 10/2009 |
| WO | WO2010009989 | 1/2010 |
| WO | WO2010045163 | 4/2010 |
| WO | WO2011075871 A1 | 6/2011 |

OTHER PUBLICATIONS

Co-pending Application: Applicant: Carnali et al., U.S. Appl. No. 13/155,451, filed Jun. 8, 2011.
Co-pending Application: Applicant: Lou et al., U.S. Appl. No. 12/855,348, filed Aug. 3, 2011.
Co-pending Application: Applicant: Carnali et al., U.S. Appl. No. 12/909,874, filed Oct. 22, 2010.
Co-pending Application: Applicant: Shah et al., U.S. Appl. No. 61/561,307, filed Nov. 18, 2011.
Co-pending Applicatin: Applicant: Shah et al., U.S. Appl. No. 61/569,826, filed Dec. 13, 2011.
PCT International Search Report in PCT application PCT/CN2010/001964 and Written Opinion dated Sep. 15, 2011.
PCT International Search Report in PCT application PCT/EP2009/053578 and Written Opinion dated Jul. 29, 2009.
PCT International Search Report in PCT application PCT/EP2020/52710 and Written Opinion dated Jul. 27, 2010.
PCT International Search Report in PCT application PCT/EP2010/068073 dated Jul. 25, 2011.
PCT International Search Report in PCT application PCT/CN2010/00864 and Written Opinion dated Mar 24, 2011.
GB Search Report in GB application GB 1113318.8 dated Nov. 7, 2011.
GB Search Report in GB application GB 111661.8 dated Jan. 16, 2010.
PCT International Search Report in PCT application PCT/CN2009/001544 dated Oct. 28, 2010.

* cited by examiner

COMPOSITIONS AND METHODS FOR IMPARTING A SUNLESS TAN WITH FUNCTIONALIZED ADJUVANTS

FIELD OF THE INVENTION

The present invention is directed to a composition and method for imparting a sunless tan to skin. More particularly, the invention is directed to a composition and method that employ a sunless tanning agent as well as an adjuvant for the sunless tanning agent. The composition, when applied, unexpectedly results in the consumer having skin with an improved and longer lasting brownish/tan coloration within a consumer acceptable time. The adjuvants of the present invention are preferably pyrrole and/or indole derivatives functionalized with a substituent comprising a carbonyl group.

BACKGROUND OF THE INVENTION

Sunless tanning agents are formulated into two types of cosmetic products. Of these, the most traditional is the self-tanning or sunless tanning lotion. The imparted benefit is to achieve a skin coloration equivalent to that from basking in the sun. More recently, a second product category has arrived. Therein a sunless tanning agent in small amounts is added to a typical moisturizing lotion. A "glow or shine" is thereby imparted. Glow or shine is a major factor in the appearance of healthy looking skin.

Most prominent among the sunless tanning agents is dihydroxyacetone ("DHA" which is also chemically known as 1,3-dihydroxy-2-propanone). DHA, after application, is believed to exert its effect through interactions between its carbonyl group and the amino groups of amino acids and peptides naturally occurring in the hydrolipid pellicle and first layers of the stratum corneum of the skin. These so-called Maillard reactions are believed (see, e.g., Bobin et al., J. Soc. Cosmet. Chem. 35: 255 (1984)) to lead to formation of brown pigments in the skin, thereby giving it an appearance similar to that of a naturally obtained tan.

Unfortunately, many sunless tanning products available on the market are not stable in that they turn a yellow and/or orange color after application, especially when exposed to UV light. Other sunless tanning products perform poorly and do not quickly impart a noticeable brown color after application. Such poorly performing products do not prevent "tan-happy" consumers from basking in the sun. Products that underperform, therefore, do not protect consumers from the sun's ultraviolet rays.

There is increasing interest to develop compositions and methods for imparting a sunless tan, and especially, compositions that can yield fast and more natural looking tans. This invention, therefore, is directed to a composition and method that employ a sunless tanning agent as well as an adjuvant comprising pyrrole and/or indole derivatives functionalized with a substituent comprising a carbonyl group for the sunless tanning agent. The composition, when applied, unexpectedly penetrates into the skin well and results in the consumer having skin with a long and natural brownish lasting tan coloration within a consumer acceptable time.

Additional Information

Efforts have been disclosed for making self-tanning cosmetic compositions. In U.S. Pat. Nos. 5,232,688 and 5,612,044, self-tanner compositions with DHA are described.

Other efforts have been disclosed for making self-tanning compositions. In U.S. Pat. Nos. 5,750,092 and 5,756,075, compositions with DHA and secondary amines, and an apparatus and method for sunless tanning are described, respectively.

Still other efforts have been disclosed for making self-tanning compositions. In U.S. Pat. No. 6,231,837, self tanning formulations comprising DHA, polyethoxyglycol and a polyol are described.

Additional efforts have been disclosed for making self-tanning compositions. In U.S. Published Application No. 2005/0002978 A1, dual component skin care compositions that comprise a self-tanning agent are described.

None of the additional information describes a method and/or composition that yield excellent sunless tanning results whereby the composition and method employ a sunless tanning agent and an adjuvant comprising pyrrole and/or indole derivatives functionalized with a substituent comprising a carbonyl group.

SUMMARY OF THE INVENTION

In a first aspect, the present invention is directed to a composition comprising:
a) a sunless tanning agent; and
b) an adjuvant for the sunless tanning agent, the adjuvant comprising a pyrrole and/or indole derivative functionalized with a carbonyl group.

In a second aspect, the present invention is directed to a method for generating a sunless tan comprising the step of applying to the skin the composition of the first aspect of this invention.

All other aspects of the present invention will more readily become apparent upon considering the detailed description and examples which follow.

Sunless tanning, as used herein, means obtaining the suntan look by applying a topical composition. The same can be interchanged with self-tanning. Composition, as used herein, is meant to include a substance applied to a human body for imparting a sunless tan where the composition is, for example, a leave-on skin lotion, cream or mousse, shampoo, hair conditioner, shower gel, toilet bar, body wash, shaving cream, body wax, depilatory, mascara, sunscreen product or the like. Such a composition may also be put on body towelettes for application to the body. In a preferred embodiment, the composition of this invention is a lotion or cream. Consumer acceptable time means within about 3 to about 6 hours from application, and preferably, from about 1 to about 2 hours, and most preferably, from about 15 to about 30 minutes subsequent to application. Pyrrole derivative means comprising the pyrrole ring and at least one functional group such as a carboxylic acid, ester, amide, ketone or aldehyde group but not necessarily with nitrogen as the heteroatom in the ring. Indole derived means comprising the indole double ring structure and at least one functional group such as a carboxylic acid, ester, amide, ketone or aldehyde group but not necessarily with nitrogen as the heteroatom in the ring. In a preferred embodiment, only one functionalized group is present on the pyrrole and indole derivatives. In a most preferred embodiment, the one functionalized group is a carboxylic acid group. Assessing color means visually analyzing color changes and/or analyzing color change with a colorimeter such as a HunterLab Labscan XE colorimeter where darkness or lightness of a color is observed over a course of time on an achromatic basis.

Comprising, as used herein, is meant to include consisting essentially of and consisting of. All ranges identified herein are meant to include all ranges subsumed therein if, for example, reference to the same is not explicitly made.

DETAILED DESCRIPTION OF THE INVENTION

The sunless tanning agent suitable for use in this invention is only limited to the extent that it may be applied topically on humans to form pigmented components. Such materials may be alpha-hydroxyaldehydes and ketones, glyceraldehyde, troxerutin and related alcohol aldehydes, various indoles, imidazoles and derivatives thereof.

Illustrative yet non-limiting examples of the sunless tanning agents that may be used in this invention include dihydroxyacetone, melanin, mahakanni (eclipta alba), methyl glyoxal, erythrulose, alloxan, 2,3-dihydroxysuccindialdehyde, mixtures thereof, or the like. In a preferred embodiment, the sunless tanning agent used is dihydroxyacetone, erythrulose or a mixture thereof. In a most preferred embodiment, the sunless tanning agent is dihydroxyacetone.

Typically, the sunless tanning agent makes up from about 0.025 to about 35%, and preferably, from about 0.05 to about 15%, and most preferably, from about 0.5 to about 10% by weight of the composition, based on total weight of the composition and including all ranges subsumed therein.

The adjuvant (i.e., pyrrole and/or indole derivative functionalized with a group comprising a carbonyl group) that may be used in this invention is limited only to the extent that the same may be used in a composition suitable for topical application to humans.

Typically, such adjuvants are generally represented by the formula(e):

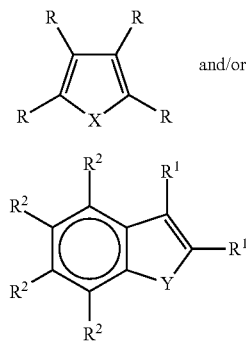

wherein each R and $R^1$ are independently hydrogen, $C_{1-6}$ alkyl, $C_{1-3}$ alkoxy group, aryl, heteroaryl or

where $R^*$ is H, $C_{1-3}$ alkyl, $N(R^{})_2$ or $OR^{}$ and further where each $R^{**}$ is independently H or a $C_{1-4}$ alkyl;
each $R^2$ is independently H or a $C_{1-4}$ alkyl;
X and Y are each independently O, S, $NR^3$ or $C(R^3)_2$; and
each $R^3$ is independently H or a $C_{1-3}$ alkyl, aryl or heteroaryl, with the proviso that at least one R and one $R^1$ (but preferably only one R and $R^1$) are a substituent comprising a carbonyl group.

In a preferred embodiment, the sunless tanning adjuvant used in this invention is 1-methyl-2-pyrrolecarboxylic acid, 1H-indole-2-carboxylic acid, pyrrole-2-carboxylic acid or a mixture thereof. In an often most preferred embodiment, the sunless tanning adjuvant used is 1-methyl-2-pyrrolecarboxylic acid. Typically, the adjuvant makes up from about 0.025 to about 35%, and preferably, from about 0.05 to about 15%, and most preferably, from about 0.5 to about 8% by weight of the composition, including all ranges subsumed therein. Moreover, where possible, salts such as Na, K, Li, Mg and/or Ca salts of the adjuvants may be used in this invention.

Compositions of the present invention will typically include a cosmetically acceptable carrier. Water is the most preferred carrier. Amounts of water may range from about 1 to about 99%, and preferably, from about 5 to about 90%, and most preferably, from about 35 to about 80% and optimally from about 40 to about 75% by weight, based on total weight of the composition and including all ranges subsumed therein. Ordinarily the compositions will be water and oil emulsions, most preferably, of the oil-in-water variety. Water-in-oil emulsions, and especially, those generally classified as water-in-oil and high internal phase emulsions are, however, an option. Illustrative examples of the high internal phase emulsions suitable to carry the actives and adjuvants of this invention described in commonly owned U.S. Patent Application Publication Nos. 2008/0311058 and 2009/0247445, the disclosures of which are incorporated herein by reference.

Other cosmetically acceptable carriers may include mineral oils, silicone oils, synthetic or natural esters, fatty acids and alcohols. Amounts of these materials may range from about 0.1 to about 50%, and preferably, from about 0.1 to about 30%, and most preferably, from about 1 to about 20% by weight of the composition, including all ranges subsumed therein.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, and preferably, from about 4 to about 5 silicon atoms.

Linear volatile silicone materials generally have viscosities less than about 5 centistokes at 25° C. while cyclic materials typically have viscosities of less than about 10 centistokes. Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from about 5 to about 100,000 centistokes at 25° C.

An often preferred silicone source is a cyclopentasiloxane and dimethiconol solution.

Among suitable esters are:
(1) Alkenyl or alkyl esters of fatty acids having 10 to 20 carbon atoms like isopropyl palmitate, isopropyl isostearate, isononyl isonanonoate, oleyl myristate, oleyl stearate, and oleyl oleate;
(2) Ether-esters such as fatty acid esters of ethoxylated fatty alcohols;
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl mono-stearate, 1,3-butylene glycol monostearate, 1,3-butylene glycol distearate, polyoxyethylene polyol fatty acid ester, sorbitan fatty acid esters, and polyoxy-ethylene sorbitan fatty acid esters;

(4) Wax esters such as beeswax, spermaceti, myristyl myristate, stearyl stearate; and (5) Sterol esters, of which soya sterol and cholesterol fatty acid esters are examples thereof.

Fatty acids having from 10 to 30 carbon atoms may be included in the compositions of this invention. Illustrative of this category are pelargonic, lauric, myristic, palmitic, stearic, isostearic, oleic, linoleic, ricinoleic, arachidic, behenic and erucic acids.

Emulsifiers may be present in the compositions of the present invention. Total concentration of the emulsifier may range from about 0.1 to about 40%, and preferably, from about 1 to about 20%, and most preferably, from about 1 to about 5% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Preservatives can desirably be incorporated into the compositions comprising the sunless tanning agent and adjuvant of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition, including all ranges subsumed therein.

Thickening agents may be included in compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes crosslinked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer.

Amounts of the thickener may range from about 0.001 to about 5%, and preferably, from about 0.1 to about 2%, and most preferably, from about 0.2 to about 0.5% by weight of the composition including all ranges subsumed therein.

Fragrances, fixatives and abrasives may optionally be included in compositions of the present invention. Each of these substances may range from about 0.05 to about 5%, preferably between 0.1 and 3% by weight.

To enhance skin moisturization, cationic ammonium compounds may optionally be used in the compositions of this invention. Such compounds include salts of hydroxypropyltri ($C_1$-$C_3$ alkyl)ammonium mono-substituted-saccharide, salts of hydroxypropyltri($C_1$-$C_3$ alkyl)ammonium mono-substituted polyols, dihydroxypropyltri($C_1$-$C_3$ alkyl)ammonium salts, dihydroxypropyldi($C_1$-$C_3$ alkyl)mono(hydroxyethyl) ammonium salts, guar hydroxypropyl trimonium salts, 2,3-dihydroxypropyl tri($C_1$-$C_3$ alkyl or hydroxalkyl)ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

When cationic ammonium compounds are used, preferred additives for use with the same are moisturizing agents such as substituted ureas like hydroxymethyl urea, hydroxyethyl urea, hydroxypropyl urea; bis(hydroxymethyl)urea; bis(hydroxyethyl)urea; bis(hydroxypropyl)urea; N,N'-dihydroxymethyl urea; N,N'-di-hydroxyethyl urea; N,N'-di-hydroxypropyl urea; N,N,N'-tri-hydroxyethyl urea; tetra (hydroxymethyl)urea; tetra(hydroxyethyl)urea; tetra (hydroxypropyl)urea; N-methyl-N'-hydroxyethyl urea; N-ethyl-N'-hydroxyethyl urea; N-hydroxypropyl-N'-hydroxyethyl urea and N,N'dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from about 0.01 to about 20%, and preferably, from about 0.5 to about 15%, and most preferably, from about 2 to about 10% based on total weight of the composition and including all ranges subsumed therein.

When cationic ammonium compound and substituted urea are used, in a most especially preferred embodiment at least from about 0.01 to about 25%, and preferably, from about 0.2 to about 20%, and most preferably, from about 1 to about 15% humectant, like glycerine, is used, based on total weight of the composition and including all ranges subsumed therein.

Conventional humectants may be employed in the present invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 50%, preferably between 1 and 15% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the end use composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the end use composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary.

Also optionally suitable for use include materials like lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Conventional buffers/pH modifiers may be used. These include commonly employed additives like sodium hydroxide, hydrochloric acid, citric acid and citrate/citric acid buffers. In an especially preferred embodiment, the pH of the composition of this invention is from about 3 to about 4.75, and preferably, from about 3.25 to about 4, and most preferably, from about 3.25 to about 3.75, including all ranges subsumed therein.

Colorants, opacifiers, chelators (like tetrasodium EDTA) and abrasives may also be included in the compositions of the present invention. Each of these substances may range from about 0.05 to about 5%, preferably between 0.1 and 3% by weight of the composition.

In an especially preferred embodiment, the composition of the present invention comprises less than 5%, and preferably, from 0.01 to 4% glycine, and most preferably, no glycine. In another especially preferred embodiment, the composition of the present invention comprises less than 5%, and preferably, from 0.1 to 4% by weight amino acid, and most preferably, no amino acid.

A wide variety of packaging can be employed to store and deliver the compositions. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

Optionally, the composition of this invention may be divided so that a first portion may carry sunless tanning agent and a second portion may carry adjuvant. When dividing the composition, each portion should be packaged separately from each other and not come into contact with each other until application to the body. The packaging for dual compositions is known and commercially available. Upon application, the make up of the composition (i.e., the combined portions) is as described herein.

When making the composition of the present invention, ingredients may be combined in no particular order. Typically the ingredients are combined and mixed under conditions of moderate shear and at ambient temperature with pressure being atmospheric conditions. In a most preferred embodiment, DHA and adjuvant are not added at a time when mixing and heating are desired. When applied by the consumer, typically from about 1 to 5 mg, and preferably, from about 1 to 4 mg, and preferably, from about 1.5 to 2.5 mg per square centimeter of composition is applied to body surface (like skin) and including all ranges subsumed therein.

The following examples are provided to facilitate an understanding of the present invention. The examples are not intended to limit the scope of the claims.

EXAMPLE 1

A control solution was made as follows: Mixing vials were charged with 2.5 weight percent glycine, 2.5 percent by weight DHA and 0.2 M citric/citrate buffer solution to produce the desired control solution, pH 5.6. The balance of the control solutions was water. Compositions consistent with the invention were made as follows: about 0.5 to 2.0 weight percent adjuvant, 2.5 weight percent DHA and 2.5 weight percent glycine were combined, resulting in compositions consistent with this invention with water as the balance. The initial pH of the resulting adjuvant comprising solution was measured and adjusted with NaOH or citric acid, if necessary, to yield an adjuvant comprising solution, pH of about 5.6. The solutions were placed in a 35° C. oven and color change was assessed visually (by taking photos) and by measuring L*a*b* values utilizing a conventional colorimeter. L*a*b* values of the solutions were measured and assessed as set forth below.

General procedure for in vitro testing: DHA, 2.5 weight percent, and 0.5 to 2.0 weight percent adjuvant were formulated into the base (as described in Table 1). About 20 mg of resulting composition was applied to VitroSkin® made available from IMS Company and applied in a circular pattern having a diameter around 2.4 cm. The artificial skin was pre-hydrated under 50% RH for 24 hours before use, and the skin was kept at a temperature of 35° C. under constant relative humidity (RH, 50%). Color development was evaluated with a colorimeter as defined below.

TABLE 1

| Ingredient | Wt. % |
| --- | --- |
| Sodium hydroxypropyl starch phosphate | 0.10 |
| Chelators | 0.11 |
| Preservative | 0.3 |
| Glycerin | 12.0 |
| Citric acid* | 0.1–0.2 |
| Colorant | 0.19 |
| Stearic acid | 1.97 |
| Emulsifier | 4.2 |
| Cetyl alcohol | 0.31 |
| Isopropyl palmitate | 2.25 |
| Silicone oil | 1.5 |
| Phenoxyethanol | 0.4 |
| Perfume | 0.35 |
| Dihydroxyacetone | 2.5 |
| Adjuvants | 0.5 to 2.0 |
| Deionized water | balance |

*to pH 3.30

Pyrrole-2-carboxylic Acid Enhancement in DHA Containing Solution

Enhancement activity of pyrrole-2-carboxylic acid in solution was carried out on the solutions described in Table 2 and the color of the reaction system was detected and assessed with a colorimeter.

TABLE 2

| Samples | DHA (wt. %) | Glycine (wt. %) | Pyrrole-2-carboxylic acid (wt. %) |
| --- | --- | --- | --- |
| 1 (Control) | 2.5 | 2.5 | — |
| 2 | 2.5 | 2.5 | 0.5 |
| 3 | 2.5 | 2.5 | 1 |
| 4 | 2.5 | 2.5 | 2 |

Color transformation results for the solutions are shown in Table 3. Delta L* was used to characterize color change whereby the larger Delta L* value reflects darker coloring. The results show that pyrrole-2-carboxylic acid significantly enhanced DHA activity at all concentrations tested. Pyrrole-2-carboxylic acid, therefore, is believed to catalyze the DHA/glycine Maillard reaction. Moreover, the platform of curves obtained when using pyrrole-2-carboxylic acid were much higher than that of the control, unexpectedly indicating that the color produced is much darker when DHA is formulated with pyrrole-2-carboxylic acid, an adjuvant consistent with this invention.

TABLE 3

Enhancement activity test results for pyrrole-2-carboxylic acid in solution from 22 to 77 hours.

| | delta L* | | |
| --- | --- | --- | --- |
| Sample | 22 hours | 51 hours | 77 hours |
| 1 (Control) | 17 | 30.81 | 37.4 |
| 2 | 18.53 | 39.39 | 51.19 |
| 3 | 23.75 | 53.05 | 68.09 |
| 4 | 29.07 | 67.52 | 85.2 |

Enhancement activity of pyrrole-2-carboxylic acid was carried out on artificial skin when formulated in a ready-to-use composition with ingredients as described in Table 4 and color was detected and assessed with a colorimeter.

TABLE 4

Enhancement activity testing for pyrrole-2-carboxylic acid comprising compositions on artificial skin

| Samples | DHA (wt. %) | Pyrrole-2-carboxylic acid (wt. %) |
| --- | --- | --- |
| 5 (Control) | 2.5 | — |
| 6 | 2.5 | 0.5 |
| 7 | 2.5 | 1 |
| 8 | 2.5 | 2 |

The results are summarized in Table 5 and the same unexpectedly show that pyrrole-2-carboxylic acid resulted in DHA color enhancement activity at all tested concentrations on artificial skin.

TABLE 5

Enhancement activity test results for pyrrole-2-carboxylic acid on VitroSkin testing from 6 to 74 hours

| | delta L* | | | |
| --- | --- | --- | --- | --- |
| Samples | 6 hours | 29 hours | 50 hours | 74 hours |
| 5 (Control) | 7.12 | 15.95 | 17.27 | 18.2 |
| 6 | 8.26 | 18.06 | 19.79 | 20.74 |
| 7 | 8.58 | 18.12 | 20.66 | 21.39 |
| 8 | 8.63 | 18.54 | 20.88 | 22.17 |

Additionally, the quality of color produced with these samples was compared in terms of delta a*/delta b* values. The color produced by DHA in the absence of adjuvant was yellowish in comparison to a traditional suntan. The results in Table 6 show how adjuvant consistent with this invention influences color over time in hours. The results demonstrate that the delta a*/delta b* value of the control quickly increased to a maximum value then decreased gradually with reaction time. Larger delta a*/delta b* values were obtained when pyrrole-2-carboxylic acid was added to the reaction system, giving rise to a higher maximum value and a slower rate of decrease than the control in the same reaction time period. These results surprisingly indicate that pyrrole-2-carboxylic acid resulted in longer lasting and more natural color when formulated with DHA in a ready-to-use composition.

TABLE 6

| | delta a*/delta b* | | | |
|---|---|---|---|---|
| Samples | 6 hours | 29 hours | 50 hours | 74 hours |
| 5 (Control) | 0.33 | 0.31 | 0.27 | 0.25 |
| 6 | 0.33 | 0.33 | 0.31 | 0.29 |
| 7 | 0.30 | 0.33 | 0.31 | 0.30 |
| 8 | 0.35 | 0.34 | 0.32 | 0.31 |

EXAMPLE 2

The solutions and compositions made in this Example (described in Table 7) were made and tested in a manner similar to the one described in Example 1 except that 1-methyl-2-pyrrolecarboxylic acid was used as the adjuvant in lieu of pyrrole-2-carboxylic acid.

TABLE 7

Enhancement activity testing for 1-methyl-2-pyrrolecarboxylic acid in solution

| Samples | DHA (wt. %) | Glycine (wt. %) | 1-methyl-2-pyrrolecarboxylic acid (wt. %) |
|---|---|---|---|
| 9 (Control) | 2.5 | 2.5 | — |
| 10 | 2.5 | 2.5 | 0.5 |
| 11 | 2.5 | 2.5 | 1 |
| 12 | 2.5 | 2.5 | 2 |

The data in Table 8 demonstrates that 1-methyl-2-pyrrolecarboxylic acid unexpectedly resulted in excellent DHA enhancement activity in solution. The final color was measured and assessed with a colorimeter. Delta L* values obtained over time (22.5-160 hours) revealed excellent color darkening when DHA was formulated with adjuvant.

TABLE 8

Enhancement activity testing results for 1-methyl-2-pyrrolecarboxylic acid in solution

| | delta L* | | | | |
|---|---|---|---|---|---|
| Samples | 22.5 h | 47 h | 87 h | 111 h | 160 h |
| 9 (Control) | 18.47 | 29.31 | 45.78 | 49.06 | 52.23 |
| 10 | 33.61 | 53.28 | 69.53 | 70.83 | 73.12 |
| 11 | 32.67 | 53.3 | 72.61 | 74.71 | 77.66 |
| 12 | 35.39 | 55.13 | 75.34 | 78.19 | 81.96 |

Enhancement activity of 1-methyl-2-pyrrolecarboxylic acid was carried out on artificial skin when formulated in a ready-to-use composition with ingredients as described in Table 9 and color was detected and assessed with a colorimeter.

TABLE 9

Enhancement activity testing for 1-methyl-2-pyrrolecarboxylic acid comprising compositions on artificial skin

| Samples | DHA (wt. %) | 1-methyl-2-pyrrolecarboxylic acid (wt. %) |
|---|---|---|
| 9 (Control) | 2.5 | — |
| 10 | 2.5 | 0.5 |
| 11 | 2.5 | 1 |
| 12 | 2.5 | 2 |

The results are summarized in Table 10 and the same unexpectedly show that 1-methyl-2-pyrrolecarboxylic acid resulted in color enhancement activity (and more natural color via visual examination) at all tested concentrations on artificial skin and when formulated in a ready-to-use composition.

TABLE 10

Enhancement activity testing for 1-methyl-2-pyrrolecarboxylic acid on VitroSkin testing from 16 to 112 hours

| | delta L* | | | |
|---|---|---|---|---|
| Samples | 21 hours | 40 hours | 88 hours | 112 hours |
| 9 (Control) | 11.75 | 14.18 | 15.71 | 15.62 |
| 10 | 12.99 | 15.91 | 17.37 | 17.4 |
| 11 | 15.42 | 19.69 | 19.7 | 12 |
| 12 | 17.24 | 19.76 | 21.18 | 21.15 |

Color quality was also characterized by assessing the delta a*/delta b* values as shown in Table 11. The data, obtained with a colorimeter for compositions formulated with 1-methyl-2-pyrrolecarboxylic acid was better than that of the control at all concentrations tested.

TABLE 11

| | delta a*/delta b* | | | | |
|---|---|---|---|---|---|
| Samples | 16 h | 21 h | 40 h | 88 h | 112 h |
| 9 (Control) | 0.35 | 0.33 | 0.28 | 0.23 | 0.23 |
| 10 | 0.37 | 0.35 | 0.30 | 0.25 | 0.25 |
| 11 | 0.38 | 0.36 | 0.31 | 0.28 | 0.27 |
| 12 | 0.39 | 0.37 | 0.33 | 0.29 | 0.29 |

The results in Table 10 and 11 unexpectedly reveal that 1-methyl-2-pyrrolecarboxylic acid is surprisingly an excellent DHA enhancer that results in a faster but natural sunless tan.

EXAMPLE 3

Solutions and compositions made with 1H-indole-2-carboxylic acid were made in the manner described in Example 1. Enhancement activity of 1H-indole-2-carboxylic acid in solution was conducted on the solutions and the resulting data is depicted in Table 12.

TABLE 12

Enhancement activity testing for 1H-indole-2-carboxylic acid in solution

| Samples | DHA (wt. %) | Glycine (wt. %) | 1-H-indole-2-pyrrolecarboxylic acid (wt. %) |
|---|---|---|---|
| 13 (Control) | 2.5 | 2.5 | — |
| 14 | 2.5 | 2.5 | 0.5 |
| 15 | 2.5 | 2.5 | 1 |
| 16 | 2.5 | 2.5 | 2 |

The delta L* data in Table 13 shows that 1H-indole-2-carboxylic acid as an adjuvant in solution with DHA resulted, unexpectedly, in excellent color enhancement.

TABLE 13

Enhancement activity results for 1H-indole-
2-carboxylic acid in solution with DHA

| Samples | delta L* | | | |
|---|---|---|---|---|
| | 2 h | 4 h | 28 h | 75 h |
| 13 (Control) | 0.35 | 1.2 | 19.56 | 33.49 |
| 14 | 0.08 | 0.95 | 19.46 | 36.83 |
| 15 | 0.15 | 1.9 | 21.46 | 38.41 |
| 16 | −1.61 | 6.66 | 26.14 | 47.82 |

The data obtained with a colorimeter over a period of 2 to 75 hours reveals that 1-H-indole-2-carboxylic acid, unexpectedly results in excellent coloring properties. The negative result for Sample 16 at 2 hours is the result of instrument variability and not consistent with the trend established at longer times.

EXAMPLE 4

Solutions and compositions made with methyl-2-pyrrole carboxylate, 2-acetylpyrrole and 2-acetyl-1-methylpyrrole were made in a manner similar to the one described in Example 1. Enhancement activity of the adjuvants in solution was assessed with ingredients as defined in Table 14.

TABLE 14

Enhancement activity testing of solutions with adjuvants and DHA

| | Wt. % | | | | |
|---|---|---|---|---|---|
| Samples | DHA | glycine | methyl 2-pyrrole carboxylate | 2-acetyl-pyrrole | 2-acetyl-1-methylpyrrole |
| 17 (Control) | 2.5 | 2.5 | — | | |
| 18 | 2.5 | 2.5 | 0.5 | | |
| 19 | 2.5 | 2.5 | 1 | | |
| 20 | 2.5 | 2.5 | 2 | | |
| 21 | 2.5 | 2.5 | | 0.5 | |
| 22 | 2.5 | 2.5 | | 1 | |
| 23 | 2.5 | 2.5 | | 2 | |
| 24 | 2.5 | 2.5 | | | 0.5 |
| 25 | 2.5 | 2.5 | | | 1 |
| 26 | 2.5 | 2.5 | | | 2 |

TABLE 15

Enhancement activity results for adjuvants in solution with DHA

| | | delta L* | | |
|---|---|---|---|---|
| Samples | | 20 h | 45 h | 75 h |
| 17 (Control) | | 15.32 | 28.03 | 33.49 |
| methyl 2-pyrrole carboxylate | 18 | 15.49 | 29.64 | 37.29 |
| | 19 | 15.64 | 30.26 | 38.59 |
| | 20 | 16.27 | 30.9 | 39.77 |
| 2-acetylpyrrole | 21 | 17.48 | 31.94 | 54.82 |
| | 22 | 17.64 | 32.17 | 55.68 |
| | 23 | 19.47 | 34.67 | 59.85 |
| 2-acetyl-1-methylpyrrole | 24 | 17.9 | 32.21 | 54.67 |
| | 25 | 18.66 | 33.22 | 56.05 |
| | 26 | 19.04 | 33.47 | 56.33 |

The delta L* data in Table 15 unexpectedly shows that methyl-2-pyrrole carboxylate, 2-acetylpyrrole and 2-acetyl-1-methylpyrrole are excellent adjuvants in solution with DHA, resulting in surprisingly good color enhancement (as determined with a colorimeter).

EXAMPLE 5

Enhancement activity of 2-acetylpyrrole, 2-acetyl-1-methylpyrrole, 2-acetylfuran and 2-furoic acid in solution were carried out on the artificial skin with ingredients as described in Table 16. Color was detected and assessed with a colorimeter for the compositions made and having a base similar to the base described in Table 1.

TABLE 16

| | Wt. % | | | | |
|---|---|---|---|---|---|
| Samples | DHA | 2-acetyl-pyrrole | 2-acetyl-1-methylpyrrole | 2-acetyl-furan | 2-furoic acid |
| 27 (Control) | 2.5 | — | | | |
| 28 | 2.5 | 0.5 | | | |
| 29 | 2.5 | 1 | | | |
| 30 | 2.5 | 2 | | | |
| 31 | 2.5 | | 0.5 | | |
| 32 | 2.5 | | 1 | | |
| 33 | 2.5 | | 2 | | |
| 34 | 2.5 | | | 0.5 | |
| 35 | 2.5 | | | 1 | |
| 36 | 2.5 | | | 2 | |
| 37 | 2.5 | | | | 0.5 |
| 38 | 2.5 | | | | 1 |

The delta L* data in Table 17 unexpectedly shows that 2-acetypyrrole, 2-acetyl-1-methylpyrrole, 2-acetylfuran and 2-furoic acid as adjuvants in compositions with DHA resulted, unexpectedly, in color enhancement of artificial skin. Visual observations further confirmed the results obtained with a colorimeter.

TABLE 17

| | | delta L* | | |
|---|---|---|---|---|
| Samples | | 5 h | 28 h | 50 h |
| 27 (Control) | | 1.7 | 8.51 | 9.87 |
| 2-acetylpyrrole | 28 | 2.14 | 10 | 11.72 |
| | 29 | 2.17 | 10.11 | 11.68 |
| | 30 | 2.52 | 10.51 | 11.91 |
| 2-acetyl-1-methylpyrrole | 31 | 2.23 | 10.01 | 11.46 |
| | 32 | 2.42 | 10.59 | 11.72 |
| | 33 | 2.79 | 10.6 | 11.83 |
| 2-acetylfuran | 34 | 2.22 | 10.02 | 11.43 |
| | 35 | 2.8 | 11.21 | 12.61 |
| | 36 | 2.33 | 10.48 | 11.83 |
| 2-furoic acid | 37 | 1.99 | 9.24 | 11.07 |
| | 38 | 1.81 | 9.84 | 10.89 |

What is claimed is:

1. A composition comprising:
   a.) a sunless tanning agent, wherein the sunless tanning agent comprises dihydroxyacetone; and
   b.) an adjuvant for the sunless tanning agent, wherein the adjuvant is 1-methyl-2-pyrrolecarboxylic acid, 1H-indole-2-carboxylic acid, pyrrole-2-carboxylic acid, or a mixture thereof.

2. The composition according to claim 1 wherein the sunless tanning agent makes up from 0.025 to 35% by weight of the composition.

3. The composition according to claim 1 wherein the adjuvant makes up from 0.025 to 35% by weight of the composition.

4. The composition according to claim 1 wherein the composition is an emulsion.

5. The composition according to claim 1 wherein the sunless tanning agent makes up from 0.05 to 15% by weight of the composition and the adjuvant makes up from 0.05 to 15% by weight of the composition.

6. The composition according to claim 1 wherein the composition further comprises preservatives, thickening agents, fragrance, cationic ammonium compound, humectant, substituted urea, vitamin or a mixture thereof.

7. The composition according to claim 1 wherein the composition is a cream or lotion.

8. The composition according to claim 1, wherein the adjuvant is a salt.

9. A method for imparting a sunless tan to skin comprising the step of applying to skin the composition of claim 1.

* * * * *